(12) United States Patent
Canton

(10) Patent No.: US 11,682,317 B2
(45) Date of Patent: Jun. 20, 2023

(54) VIRTUAL REALITY TRAINING APPLICATION FOR SURGICAL SCRUBBING-IN PROCEDURE

(71) Applicant: Stephen Paul Canton, Pittsburgh, PA (US)

(72) Inventor: Stephen Paul Canton, Pittsburgh, PA (US)

(*) Notice: Subject to any disclaimer, the term of this patent is extended or adjusted under 35 U.S.C. 154(b) by 1240 days.

(21) Appl. No.: 16/202,549

(22) Filed: Nov. 28, 2018

(65) Prior Publication Data

US 2019/0164448 A1    May 30, 2019

Related U.S. Application Data

(60) Provisional application No. 62/591,718, filed on Nov. 28, 2017.

(51) Int. Cl.

| | |
|---|---|
| *G09B 19/00* | (2006.01) |
| *G16H 40/20* | (2018.01) |
| *A61B 34/10* | (2016.01) |
| *A61B 90/00* | (2016.01) |
| *G16H 10/20* | (2018.01) |
| *G06V 20/20* | (2022.01) |

(Continued)

(52) U.S. Cl.
CPC ........... *G09B 19/003* (2013.01); *A61B 34/10* (2016.02); *A61B 90/37* (2016.02); *G06V 20/20* (2022.01); *G06V 40/23* (2022.01); *G09B 19/0076* (2013.01); *G16H 10/20* (2018.01); *G16H 40/20* (2018.01); *A61B 2034/102* (2016.02); *A61B 2090/365* (2016.02); *G16H 20/40* (2018.01)

(58) Field of Classification Search
CPC .. G09B 19/003; G09B 19/0076; A61B 34/10; A61B 90/37; A61B 2034/102; A61B 2090/365; G16H 10/20; G06V 20/20; G06V 40/23
See application file for complete search history.

(56) References Cited

U.S. PATENT DOCUMENTS

| | | | |
|---|---|---|---|
| 2002/0015716 A1* | 2/2002 | Jampani | A61K 8/898 424/401 |
| 2014/0081659 A1* | 3/2014 | Nawana | A61B 5/4833 705/3 |

(Continued)

OTHER PUBLICATIONS

Thangaratinam, et al., "The Dephi Technique", Royal College of Obstetricians and Gynacologists, 2005, 7:120-125.

*Primary Examiner* — Michelle Chin
(74) *Attorney, Agent, or Firm* — Dentons Cohen & Grigsby P.C.

(57) ABSTRACT

Disclosed herein are immersive virtual and/or augmented reality education/training tools useable to teach operating room personnel any or all of scrubbing-in procedures, gowning/gloving procedures, and proper operating room etiquette. The training tools provide individuals with active practice in the operating room setting prior to the real-world applications, and thus allows the user to become more adept with the necessary procedures prior to entering the operating room. The disclosed virtual and/or augmented reality training will make for a better, less stressful, risk-reducing (e.g., infection of patient), operating room environment that is more conducive for both learning by the students and surgical performance by the experienced operating room personnel.

19 Claims, 3 Drawing Sheets

(51) Int. Cl.
  *G06V 40/20*  (2022.01)
  *G16H 20/40*  (2018.01)

(56) References Cited

U.S. PATENT DOCUMENTS

| | | | |
|---|---|---|---|
| 2015/0302769 A1* | 10/2015 | Johnson | G09B 19/0076 |
| | | | 434/308 |
| 2017/0213473 A1* | 7/2017 | Ribeira | G09B 5/10 |
| 2018/0357886 A1* | 12/2018 | Tavori | G16H 40/20 |

* cited by examiner

VIRTUAL REALITY TRAINING APPLICATION FOR SURGICAL SCRUBBING-IN PROCEDURE

CROSS REFERENCE TO RELATED APPLICATIONS

The present application claims the benefit under 35 U.S.C. § 119(e) of prior U.S. Provisional Application No. 62/591,718 filed Nov. 28, 2017, the disclosure being incorporated herein by reference in its entirety.

TECHNICAL FIELD

This invention pertains generally to a software application providing interactive training tools, and more specifically to a virtual/augmented reality assisted learning aid that provides enhanced training for the surgical scrubbing-in and gowning/gloving procedures and proper operating room etiquette.

BACKGROUND

Many healthcare professionals and healthcare professionals-in-training hold positions that entail performing in an operating room (OR). This includes but is not limited to physicians/surgeons, residents, medical students, nurses, nursing students, operating room technicians, and operating room technician students. The operating room must be an environment that allows for the fluid, efficient, and sterile completion of a surgical procedure. In order to ensure this, every person in the operating room must adhere to very specific procedures and operating room etiquette before, during, and after every surgery. For many, especially novices to the OR, these procedures are very difficult to learn in a real-world environment due to the fast pace and necessary exactness of the techniques. This issue (gap in knowledge) is especially true for the scrubbing, gowning and gloving procedures prior to surgery, also called the scrubbing-in procedure.

The purpose of scrubbing-in is to eliminate the controllable sources of contamination via the performance of aseptic procedures. For OR newcomers, ignorance of proper scrubbing-in procedures is common. Not only does this ignorance threaten the integrity of the operating room, but it also affects the natural flow of the operating room protocol causing stress upon the trainees and the experienced OR personnel.

Prior methods for training have included detailed written protocols, and/or videos of the procedure. Neither, however, provides actual hands-on experience that may simulate the physical and psychological environment of the OR. The concept of simulation of critical events to hone skills, in contrast to mere book learning, has long been a staple of human training methodology. At its heart, the goal of simulation is to truly mimic the physical and psychological experience of an event, thus harnessing the power of emotional context and psychological stress to retain both physical and intellectual skills and lessons with more reliability than reading about or viewing the procedure alone can yield.

Various industries have adopted and refined simulation-based training methodologies, attempting to replicate work environments as precisely and accurately as possible to prepare students and professionals for critical events they may encounter in practice. In the aviation industry, for example, flight simulators have improved over time as computer technology has become more advanced and affordable. In the institution of medicine, medical scenario simulation has grown to become a standard component of medical training and continuing education, typically relying on physical "dummy" apparatuses to represent the "patients" or "subjects" of the simulation. Equipping and maintaining a state-of-the-art simulation facility employing such manikins represents a significant cost.

Simulation-based training systems that are both low cost and completely immersive are significantly limited or non-existent in many industries, and particularly in the medical industry. Accordingly, there exists a need in the art for improved training methods for medical procedures and environments such as, for example, surgical scrubbing-in procedures and the proper etiquette required in the OR environment.

SUMMARY

The presently disclosed invention provides an augmented and/or virtual reality systems and training methods for surgical scrubbing-in procedures, gowning/gloving procedures, and the proper etiquette while in the OR.

Thus, according to its major aspects, and briefly stated, the presently disclosed invention includes a computer-implemented method for providing an augmented and/or virtual reality training tool. The training tool includes generation of an augmented or virtual reality environment; detection of actions within the augmented or virtual reality environment comparison of those actions to a performance metric; and generation, based at least in part on the comparison, of a performance evaluation.

According to certain aspects of the method, the augmented or virtual reality environment may be an OR environment, and the actions may be associated with a surgical scrubbing-in procedure, a gowning/gloving procedure, and/or aseptic performance during a surgical procedure. As such, the performance metric may detect actions taken during the scrubbing-in and/or gowning/gloving procedures, such as a proper order of steps within each procedure, and the performance evaluation may define an aseptic quality of the procedures, a speed of the procedures, aseptic technique during the scrubbing-in and/or gowning/gloving procedures or a surgical procedure, or any combination thereof. The actions may be further associated with proper etiquette in the OR, and the performance metric may be detect actions taken before, during, and after a surgical procedure. According to certain aspects of the method, the actions may comprise a physical movement of a user of the system, a movement of a virtual or real object in the augmented or virtual reality environment, or any combination thereof.

The presently disclosed invention further includes a computer-implemented program product for providing the augmented or virtual reality training tool, the computer-implemented program product comprising a non-tangible computer readable medium tangibly embodying non-transitory computer-executable program instructions thereon that, when executed, cause a computing device to execute the method for providing an augmented or virtual reality training tool.

The presently disclosed invention further includes a system for providing the augmented or virtual reality training tool. The system may include a non-transitory memory comprising processor-executable instructions; and a processor coupled to the non-transitory memory and configured to execute the processor-executable instructions, wherein the processor-executable instructions comprise instructions to implement the augmented and/or virtual reality training tool.

According to certain aspects, the system may further include a display in communication with the processor, the display configured to provide visual representation of the augmented or virtual reality environment and visual feedback of the performance evaluation.

BRIEF DESCRIPTION OF THE DRAWINGS

A better understanding of the present invention will be had upon reference to the following detailed description when read in conjunction with the accompanying drawings, wherein like numerals represent like features in the various views. It is to be noted that features and components in these drawings, illustrating views of embodiments of the present invention, unless stated to be otherwise, are not necessarily drawn to scale.

DETAILED DESCRIPTION

Figure 1:
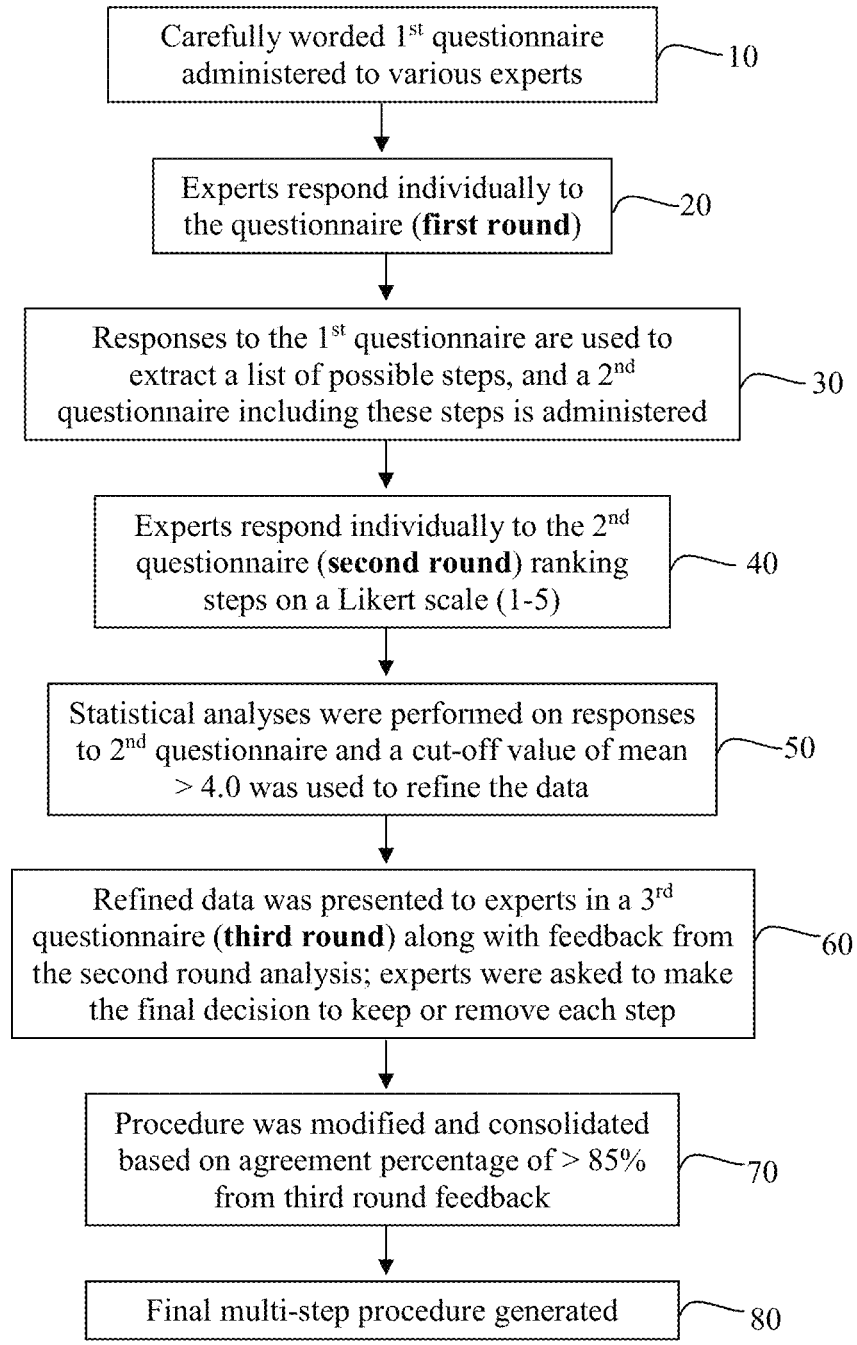
FIG. 1 is a flow diagram of steps in the Delphi process used to provide elements of the scrubbing-in and gowning/gloving procedures according to various embodiments of the presently disclosed invention.

In the following description, the present invention is set forth in the context of various alternative embodiments and implementations involving augmented and virtual reality methods and systems which provide novel learning and training tools. While the following description discloses numerous exemplary embodiments, the scope of the present patent application is not limited to the disclosed embodiments, but also encompasses combinations of the disclosed embodiments, as well as modifications to the disclosed embodiments.

Various aspects of the systems and methods may be illustrated by describing components that are coupled, attached, and/or joined together. As used herein, the terms "coupled", "attached", and/or "joined" are interchangeably used to indicate either a direct connection between two hardware components, or two software modules, or, where appropriate, an indirect connection to one another through intervening or intermediate components or modules. In contrast, when a component is referred to as being "directly coupled", "directly attached", and/or "directly joined" to another component or module, there are no intervening elements shown in said examples.

Various aspects of the systems and methods may be described and illustrated with reference to one or more exemplary implementations. As used herein, the term "exemplary" means "serving as an example, instance, or illustration," and should not necessarily be construed as preferred or advantageous over other variations of the devices, systems, or methods disclosed herein. "Optional" or "optionally" means that the subsequently described event or circumstance may or may not occur, and that the description includes instances where the event occurs and instances where it does not. In addition, the word "comprising" as used herein means "including, but not limited to".

It must also be noted that as used herein and in the appended claims, the singular forms "a", "an", and "the" include the plural reference unless the context clearly dictates otherwise. Unless defined otherwise, all technical and scientific terms used herein have the same meanings as commonly understood by one of ordinary skill in the art.

Provided herein are systems, methods, and non-transitory computer-readable media for simulation based training. This methodology uses augmented reality and/or virtual reality to greatly advance the degree of environmental and psychological fidelity available in the simulations. An augmented reality (AR) environment refers to the perception of a user of their real, physical environment with the addition of virtual, projected, two or three dimensional objects in that environment. Integral to the concept of an augmented reality environment is the feature of the virtual objects to be perceived to exist in the real space as if they were real objects, with the ability of users to walk around them and see them from different angles, as appropriate. A virtual reality (VR) environment refers to a wholly virtual, projected environment which generally includes images, sounds and other sensations to replicate a real environment or an imaginary setting, and simulates a user's physical presence in this environment to enable the user to interact with this space. In harnessing this for training, the method described enables a replication of nearly an infinite number of environments.

Establishing an augmented reality environment within a real space refers to using computer generated virtual objects projected into the space, where the virtual objects behave as if they are physically in the space, and where one or more users may be able to see each other (i.e., actual or virtual representations) and the virtual objects, and interact with the virtual objects and each other. Alternatively, virtual reality environments may be established independent of the space, and include an entirely virtual space and virtual objects. Virtual representation of one or more users may interact with each other and with the virtual space and objects therein.

A real-world operating room (OR) experience may be simulated using an immersive virtual or augmented reality. Each of the vital steps of scrubbing, gowning, and gloving may be presented step-wise allowing the user to choose the correct procedure amongst many other incorrect options. Moreover, OR etiquette may be modeled, providing an immersive training experience regarding proper interactions while in the OR. For example, standard interaction steps while in the OR may include, but are not limited to, introduction to the scrub nurse and circulating nurse, assisting with the gowning and gloving procedure (e.g., working with the nursing staff to properly dry hands and determine gown and glove size, etc.), offering to help clean up and transfer patient while still remaining sterile, being aware of what is sterile (e.g., everything that is draped with blue or resting on a blue surface), etc.

The software application may provide feedback (i.e., immediate feedback and/or delayed feedback) based on the user's selections and actions. The feedback may come in the form of virtual representations of OR personnel and/or a patient during the simulation and/or at the end of the simulation. Additionally, or alternatively, the feedback may come in the form of visual, audible, or haptic signals during the simulation and/or at the end of the simulation.

Thus, disclosed herein is an advanced medical procedure simulator which may be based on a virtual or augmented reality simulation apparatus. The simulator provides a means for medical professionals to experience the scrubbing-in procedure, the gowning/gloving procedure, and/or proper OR etiquette. The virtual or augmented reality system may compute and display a visual virtual or augmented reality model of the OR environment, and in accordance with the user's (e.g., medical professional's) gestures and actions, may provide feedback, such as visual, audible, or haptic signals.

In a virtual reality system, an entirely virtual image may be simulated for display to a user, and in an augmented reality system, a simulated image may be overlaid or otherwise incorporated with an actual image for display to the user. Various OR environments can be selected. Therefore, various different scenarios, such as would be encountered over the years by OR personnel, can be simulated for a user in a compressed period of time for training purposes. The virtual or augmented reality simulation system can also compute and provide various metrics and statistics of performance.

As used herein, the terms "virtual" and "augmented" may be used interchangeably unless specifically indicated otherwise. As such, reference to an augmented reality system may include reference to either an augmented or virtual reality system. Moreover, reference to an augmented reality display device may include reference to an augmented or virtual reality display device.

During the simulation, the user may encounter OR equipment and learn OR etiquette. The course of the simulation session may be dependent upon the actions of the user, such as button selections, voice inputs, movements of the user and/or virtual or real objects within the simulation environment, etc. Moreover, the software application may offer a consequence display representative of the user's actions (e.g. what happens to a patient or future patients if the proper procedures are not followed, such as the patient developing an infection).

Possible actions which the system of the present invention may be looking to record and compare include at least proper surgical scrubbing-in procedure, gowning/gloving procedure, and/or aseptic technique while in the OR during a surgical procedure. Such actions, or sequence of actions (steps) are a focus of the present invention, and are defined herein. These steps have been concisely defined through studies using the Delphi method, a method widely used and accepted involving a structured communication technique for achieving convergence of opinion from a panel of experts (Thangaratinam S, Redman C W. The Delphi technique. The Obstetrician & Gynaecologist. 2005; 7:120-125).

The Delphi technique facilitates an efficient group dynamic process and is done in the form of an anonymous, written, multistage survey process, where feedback of group opinion is provided after each round. In general, the Delphi technique is performed in several stages that include a first stage of convening a panel of experts about a topic of interest, such as surgeons convened to evaluate a scrubbing-in procedure. In a second stage, input from these experts, typically provided anonymously, is received in a structured way (e.g., answers to a questionnaire, an opinion on a defined problem, a set of rating scales, etc.). Evaluation of the input may be completed using a set of criteria, wherein the input may be filtered and summarized if necessary. The summarized input may then be presented to the experts in a subsequent round of evaluation (e.g., additional questionnaire), giving them an opportunity to comment and change their input based on the evaluation. This subsequent round of input may be evaluated and re-presented to the experts in a further survey round. These later steps may be iteratively repeated until the opinions of the experts are stable. It is expected that using the Delphi technique the range of the answers will decrease and converge towards consensus among the experts.

In the present invention, consensus was defined as >85% agreement among the expert panelists. For example, to determine the steps in a scrubbing-in and gowning/gloving procedure as disclosed herein, a first stage of the Delphi process was executed by convening a panel of experts from two hospitals across six different subspecialties. The panel members were chosen based on their experience as physicians in the OR, and each participated in various rounds of written survey (see Table 1).

TABLE 1

| Specialty | Round 1 | Round 2 | Round 3 |
| --- | --- | --- | --- |
| Orthopedic | 1 | 1 | 0 |
| Urology | 1 | 1 | 2 |
| Ob/Gyn | 6 | 17 | 19 |
| General | 1 | 4 | 3 |
| Plastic | 0 | 5 | 4 |
| Neurosurgery | 0 | 1 | 0 |
| Total | 9 | 29 | 28 |

With reference to FIG. 1, in a second stage of the Delphi process, two open-ended questions were administered as a written survey (step 10; first round). The survey questions were developed and reviewed by a panel of facilitators different from the survey panel of surgeons. The panelists' answers to the open ended questions served to provide a list of steps that were be used in further surveys to formulate a final list of steps for the scrubbing-in and gowning/gloving procedures. Each of the panelists responded to these questions anonymously (step 20). Their responses to this first questionnaire were then used to extract a list of more specific questions, i.e., list of steps, which were included in a second questionnaire (step 30). The panelists were then provided with this second questionnaire (step 40; second round) and asked to rank the steps on a Likert scale (1-5). A statistical analysis was performed, wherein a mean cutoff of >4.0 was used to refine the data (step 50). The refined data, i.e. shortened list of steps, was then presented to the panelists as a third questionnaire (step 60, third round), along with feedback from analysis of the second round. The panelists were asked to make a final decision to keep or remove each step from a final list of steps. This final list of steps that define the scrubbing-in procedure and/or the gowning/gloving procedure was modified and consolidated based on an agreement percentage amongst panelists of at least 85% (step 70). The final outcome of the Delphi technique is a multi-step procedure for the scrubbing-in and/or the gowning/gloving process according to the presently disclosed invention.

Figure 2:
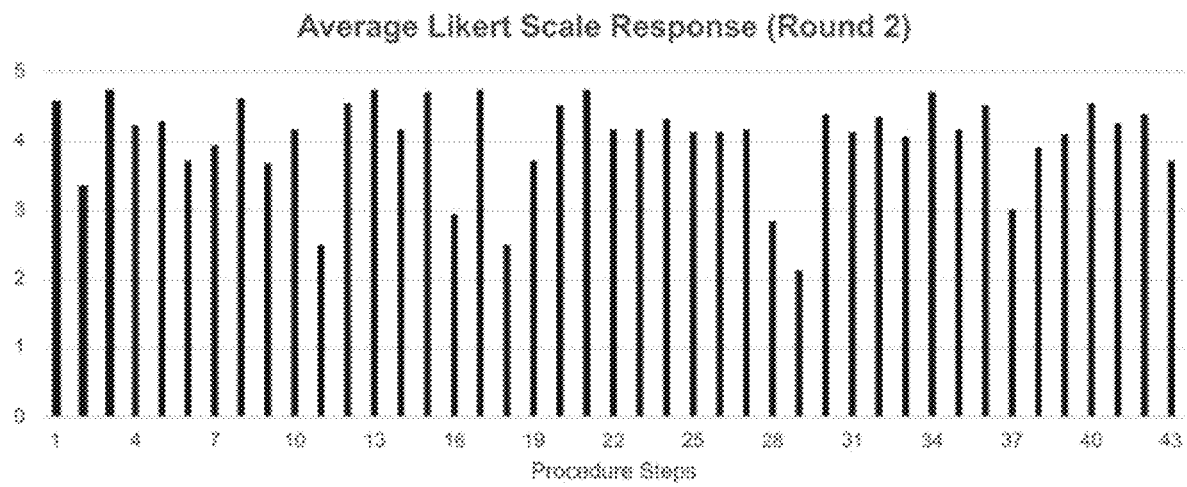
FIG. 2 shows a bar diagram of the mean of the Likert score importance value for each of the 43 steps surveyed in the second round of the survey process according to the Delphi method used in the present invention.
Figure 3:
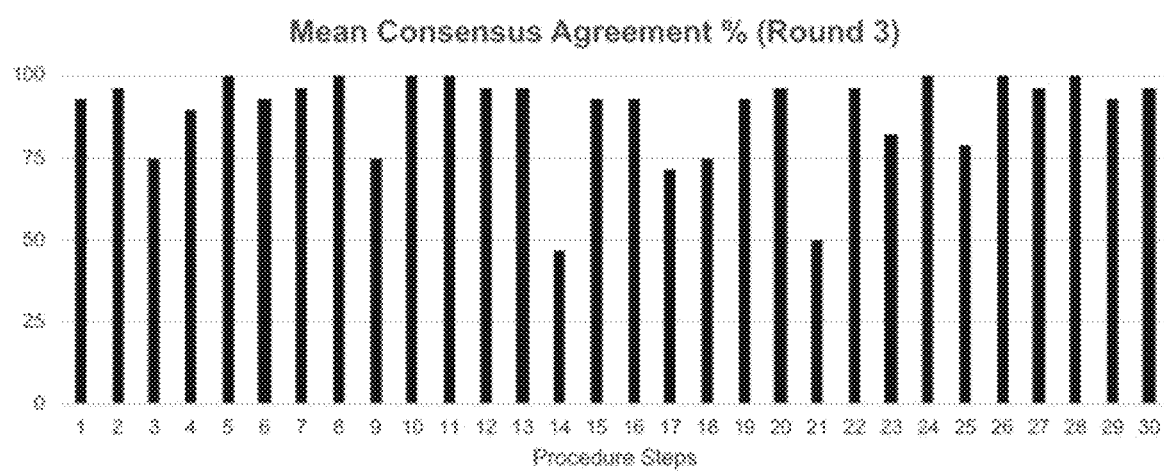
FIG. 3 shows a bar diagram of the mean consensus agreement for each of the 30 steps surveyed in the third round of the survey process according to the Delphi method used in the present invention.

In an exemplary Delphi process, as detailed herein, the first round included two open-ended questions that lead to 43 total possible steps that may define the scrubbing-in and/or gowning/gloving procedure. These 43 steps were presented to the expert panelists in a second round as detailed above, wherein the steps were ranked on a Likert score of 1-5 as shown in FIG. 2. The 30 steps having a Likert score of greater than 4.0 were then presented to the expert panelists in a third round as detailed above. These 30 steps were included/excluded from a final scrubbing-in and/or the gowning/gloving procedure. A mean consensus agreement of at least 85% for each of the 30 steps (see FIG. 3) was used to define the final 22 steps included in the multi-step procedure for the scrubbing-in and gowning/gloving process according to the presently disclosed invention.

For example, a surgical scrubbing-in procedure according to the present invention may comprise the following 10 steps performed outside of the OR, such as in a "sink room":
1. Remove jewelry from hands/arms.
2. Put on face mask and eye protection.
3. Grab and open a pre-packaged scrub/nail kit.
4. Moisten hands and arms under the water without touching the faucet.
5. Use firm (bristled) side of brush to scrub nails.
6. Use firm (bristled) end of scrub brush to scrub all surfaces of fingers and hands.
7. Use sponge to scrub the entire length of one forearm, from wrist to elbow.
8. Use sponge to scrub entire length of contralateral forearm, from wrist to elbow.
9. Rinse off both arms allowing water to fall from wrists to elbows.
10. Use back/butt/hip to enter OR keeping arms up and away from torso.

Once inside the OR, the following 12 steps may define a proper gowning and gloving procedure according to the present invention:
1. Enter OR with elevated hands/arms and approach scrub tech/nurse, taking care to avoid touching anything.
2. Hold out one hand to accept a dry towel from scrub tech/nurse.
3. Dry opposite hand/arm using the hand in which the towel was placed, from hand to elbow.
4. Flip towel to dry hand and dry opposite hand/arm that has not yet been dried, from hand to elbow.
5. With scrub tech/nurse holding gown open, place both hands/arms into sleeves allowing fingertips to come through ends of sleeves.
6. Allow nonsterile nurse/circulator to tie up back of gown.
7. With scrub tech/nurse holding right glove open, place hand into right glove.
8. With scrub tech/nurse holding left glove open, place left hand into glove.
9. Hand card (at end of gown tie) to scrub tech/nurse or circulator.
10. Rotate in gown with scrub tech/nurse or circulator still holding card.
11. Re-grasp the tie from the scrub tech/nurse or circulator.
12. Tie both ties of gown together.

Moreover, once inside the OR, proper etiquette can also be modeled using the methods and systems of the present invention. For example, proper aseptic technique during a surgical procedure may include keeping hands in the sterile field (i.e., sterile only touches sterile), wherein sterile areas of the gown are from below the neck to surgical table level. Other actions may include: never turning your back to the sterile field, remaining aware of everything that is sterile (e.g., blue drapes indicate sterile equipment/area), and always choosing to notify OR personnel if the sterile area is compromised—even if nobody is watching.

Additional actions which the system of the present invention may be looking to record and compare include at least selection of the proper surgical attire (e.g., both size and total list which may include, for example, surgical cap, shoe covers, and mask). The actions may further include, for example, performing certain tasks in the OR, such as introduction to the scrub nurse and circulating nurse, offering to obtain/open gown and gloves, proper technique to open gloves and gown from package, working together to determine glove size, setting aside phone, and writing name on whiteboard in the OR room so that OR personnel can identify you. Additional tasks may include, for example, remaining attentive to the "pre-induction verification" and "timeout" signals.

A "pre-induction verification" occurs well prior to the initiation of the surgery and is verbal acknowledgment to all personnel in the operating room about any of the following: patient id, allergies, planned procedure (state the procedure to be performed), consent correct, patient position, site marked (the side of the body and site that the procedure is to be performed), antibiotics available, implants, devices, special equipment, etc.

A "timeout" occurs immediately before the start of the procedure, subsequent procedures, and/or a new attending enters, and includes but is not limited to: patient id, correct procedure, correct site/side, correct position, antibiotic started, preparation of the site is dried, etc.

Thus, according to certain aspects, the present invention relates to a training method for a scrubbing-in procedure, wherein the method may comprise identifying, using a processor, a plurality of steps of the scrubbing-in procedure, and presenting, using an augmented reality display of an augmented reality device, a virtual representation of an OR environment. The OR environment may include a sink room of an operating room suite, and an operating room of the operating room suite. The method may include querying a user for a first step in the scrubbing-in procedure, and determining whether the first step in the scrubbing-in procedure has been completed. In response to determining that the first step has been completed, the method may further include presenting to the user a virtual representation of a subsequent step in the scrubbing-in procedure.

The method may further include, before determining the first step in the scrubbing-in procedure has been completed, determining that the first step is not being performed, or that the first step is being performed improperly. The method may then display an alert using the augmented reality display indicating that an error has occurred. The alert may be visual, audible, or haptic. According to certain aspects, the alert may be a text alert that shows within the augmented reality display, or may include other forms of alert, such audible alerts (e.g., spoken language or sound alerts).

The plurality of steps in the scrubbing-in procedure are ordered, and generally include: (1) removing jewelry from hands and arms; (2) putting on a face mask and eye protection; (3) taking and opening a pre-packaged scrub/nail kit; (4) moistening hands and arms with water from a faucet without touching the faucet; (5) using a bristled side of a brush from the pre-packaged scrub/nail kit to scrub nails; (6) using a bristled end of the brush to scrub all surfaces of fingers and hands; (7) using a sponge to scrub an entire length of one forearm, from wrist to elbow; (8) using the sponge to scrub an entire length of contralateral forearm, from wrist to elbow; (9) rinsing off both forearms allowing water to fall from wrists to elbows; and (10) using back, butt, or hip to enter the operating room while keeping arms positioned up and away from torso.

The present invention also relates to a training method for a gowning/gloving procedure, wherein the method may comprise identifying, using a processor, a plurality of steps of the gowning/gloving procedure, and presenting, using an augmented reality display of an augmented reality device, a virtual representation of an OR environment, generally including an operating room. The method may include querying a user for a first step in the gowning/gloving procedure, and determining whether the first step in the gowning/gloving procedure has been completed. In response to determining that the first step has been completed, the method may further include presenting to the user a virtual representation of a subsequent step in the gowning/gloving procedure.

The method may further include, before determining the first step in the gowning/gloving procedure has been completed, determining that the first step is not being performed, or that the first step is being performed improperly. The method may then display an alert using the augmented reality display indicating that an error has occurred.

The plurality of steps in the scrubbing-in procedure are ordered, and generally include: (1) entering the operating room environment with cleaned wet hands and arms in an elevated position, and approaching a scrub technician or nurse, taking care to avoid touching anything; (2) holding out first hand to accept a dry towel from the scrub technician or nurse; (3) drying second hand and arm using the first hand, from hand to elbow; (4) passing the towel to the second hand to dry the first hand and arm, from hand to elbow; (5) placing both hands and arms into sleeves of a gown, allowing fingertips to come through ends of sleeves, wherein the gown is held open by the scrub technician or nurse; (6) allowing a nonsterile nurse or circulator to tie a back of the gown using a first set of ties; (7) placing right hand into right glove, wherein the right glove is held open by the scrub technician or nurse; (8) placing left hand into left glove, wherein the left glove is held open by the scrub technician or nurse; (9) handing card (at end of a second tie) to the scrub technician or nurse, or to the nonsterile nurse or circulator; (10) rotating in gown with the scrub technician or nurse, or to the nonsterile nurse or circulator still holding the card (at end of the second tie); (11) re-grasping the second tie from the scrub technician or nurse, or to the nonsterile nurse or circulator; and (12) tying the second tie at front of the gown.

According to certain aspects of the invention, the method may include both the scrubbing-in and gowning/gloving procedures. As such, once each of the plurality of steps in the scrubbing-in procedure are completed, the method may include querying a user for a first step in a gowning/gloving procedure.

The present invention also includes computer implemented processes for establishing an augmented or virtual reality environment comprising an OR environment, and detecting actions of the user within the virtual or augmented reality environment, such as actions on virtual objects (i.e., generated in an AR/VR environment), or actions on real objects within a real OR environment (i.e., overlaid with a virtual OR environment such as would be generated by AR technology). These actions may be recorded and evaluated against a performance metric to define a performance evaluation for a specific procedure.

For example, in the OR environment, the procedure may comprise a scrubbing-in procedure, and the performance metric may provide a performance evaluation of an aseptic quality of the scrubbing-in procedure, a speed of the scrubbing-in procedure, performance of all steps in the scrubbing-in procedure, performance of a proper order of the steps in the scrubbing-in procedure, or a combination thereof.

Moreover, the procedure may comprise a gowning/gloving procedure, and the performance metric may provide a performance evaluation of an aseptic quality of the gowning/gloving procedure, a speed of the gowning/gloving procedure, performance of all steps in the gowning/gloving procedure, performance of a proper order of the steps in the gowning/gloving procedure, or a combination thereof.

Accordingly, the present invention provides a training system that includes a non-transitory memory comprising processor-executable instructions; and a processor coupled to the non-transitory memory and configured to execute the processor-executable instructions. The processor-executable instructions generally comprise instructions to: generate an augmented or virtual reality simulation of an operating room environment; detect, using at least one sensor, an occurrence of an action within the operating room environment; compare the action to a performance metric; and generate, based at least in part on the comparing, a performance evaluation, wherein the performance metric identifies actions taken during one or more of a scrubbing-in procedure, a gowning/gloving procedure, before a surgical procedure, during the surgical procedure, and after the surgical procedure.

The actions may be movements of the user, such as grasping a virtual scrub brush to clean the hands, or may be selections, such as using a peripheral control device (e.g., joystick, etc.) or by aiming the users gaze at a specific selectable spot within the display, such as pointing at the scrub brush or at a selection on a drop down menu. Moreover, the virtual display may represent the user in the third person, or in the first person, or may use a combination thereof through various portions of the training session.

Figure 4:
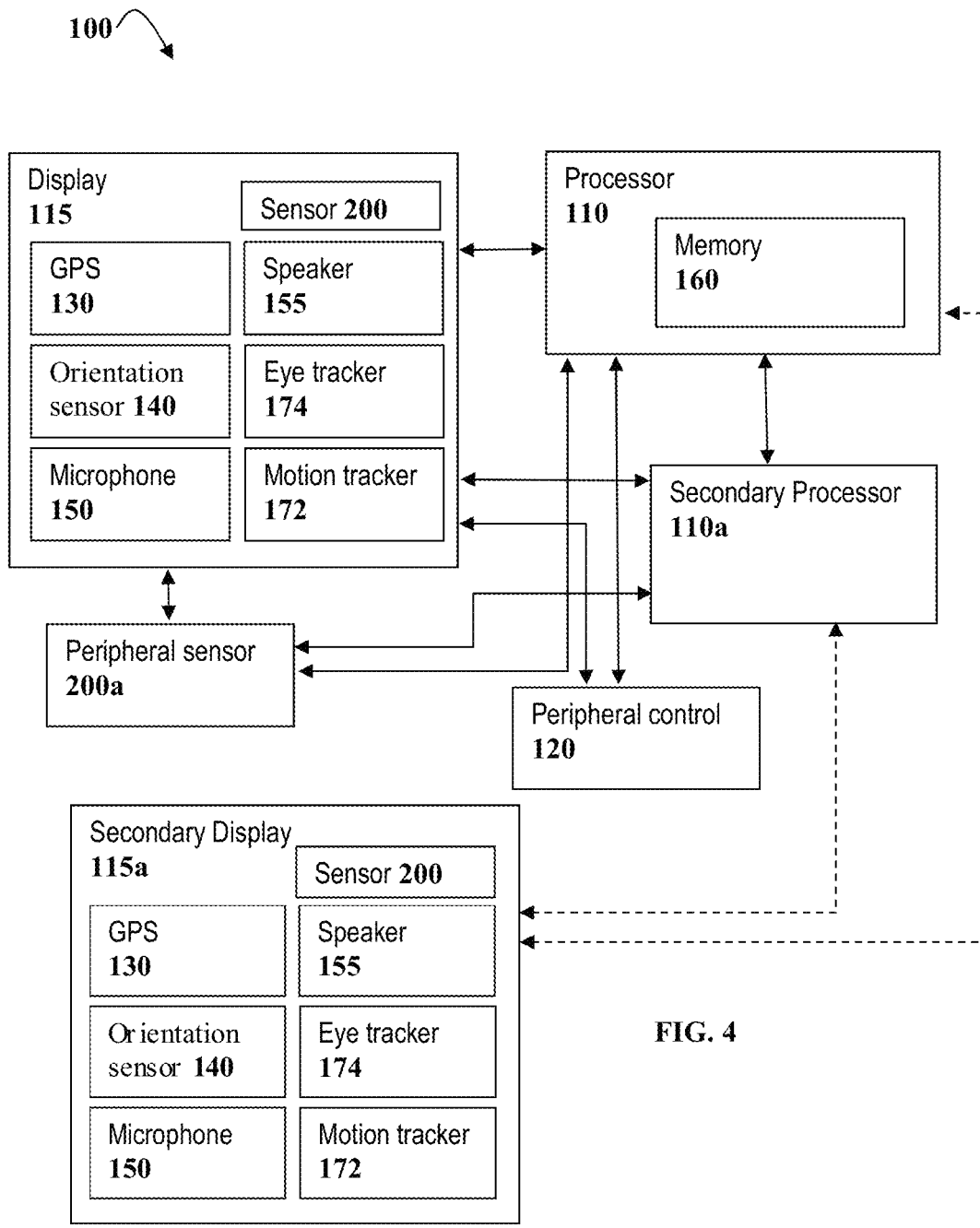
FIG. 4 is a block diagram of a training system according to various embodiments of the presently disclosed invention.

As shown in FIG. 4, a system 100 of the present invention may include a processor 110, a memory 160, and a display 115. In various embodiments, the system 100 may additionally include one or more secondary processors 110a, one or more secondary displays 115a, a peripheral control 120, a global positioning system (GPS) 130, an orientation sensor 140, a microphone 150, and/or a speaker 155. As shown in FIG. 4, each of the GPS 130, orientation sensor 140, and microphone 150 may be a part of the display 115, such as an AR/VR device, wherein the display 115 may be in electronic communication with either or both of the processors (110, 110a). Moreover, when included, the peripheral control 120 may be in electronic communication with the display 115 and/or the processor(s) (110, 110a).

The peripheral control 120 may refer to a remote control, such as a hand-held unit that may provide allow manual selection (e.g., via buttons or IR) of options. In some embodiments, the peripheral control 120 includes a joystick. The orientation sensor 140 determines the gyroscopic orientation of the user and/or display unit 115, and may enable the system to determine the angle the user is looking. The GPS 130 may be included to further aid in detecting movement of the user and/or display unit 115. The orientation sensor 140 and/or GPS 130 may be included on a plurality of suitable display devices (AR/VR devices).

The microphone 150 may enable the user to provide auditory cues when applicable to tasks performed in/on the virtual OR environment. The auditory cues received by the microphone 150 may be processed by the system and may be a source of simulation data. The speaker 155 may enable the user to receive auditory cues when applicable to tasks performed in/on the virtual OR environment.

Additional elements of the system of the present invention may include a motion tracker 172 and eye tracker 174, which may be provided to improve the immersiveness of the virtual OR environment and provide contextual data for actions performed by the user within the virtual OR environment. Moreover, one or more additional sensors (200, 200a) may be included as part of the VR/AR device, or separate from the VR/AR device. These additional sensors may be in electronic communication with the processor 110, and may provide additional information that may assist in tracking movement of the user or real objects in the augmented or virtual OR environment, or may assist in defining the OR environment (e.g., camera that may view the actual OR environment in an augmented reality simulation).

The memory 160 may be associated with the processor 110 and may store data collected by sensors (200, 200a) associated with and communicatively coupled to the display device or AR/VR device. The memory 160 may further store the processor-executable instructions used to execute the methods of the present invention. The memory 160 may additionally contain a performance metric of best practices for the user in each of the simulated procedures (e.g., scrubbing-in, gowning/gloving). The actions of the user in the virtual OR environment may be compared to and judged against this metric.

While not shown in FIG. 4, when included, the peripheral display 115a may also include a peripheral control and/or peripheral sensors.

The action within the operating room environment may comprise a physical movement of a user of the system, a movement of a real object in the operating room environment, a movement of a virtual object in the operating room environment, or any combination thereof.

The display 115 may be configured to provide a visual representation of the operating room environment. According to certain aspects, the display 115 may be configured to provide a visual feedback of the performance evaluation.

According to certain aspects, the display 115 may be an AR/VR device. The AR/VR device may include one or more screens, such as a single screen or two screens (e.g., one per eye of a user). The screens may allow light to pass through the screens such that aspects of the real environment are visible while displaying a virtual object. The virtual object may be made visible to the user by projecting light. The virtual object may appear to have a degree of transparency or may be opaque (i.e., blocking aspects of the real environment).

A user of the system may interact with the virtual object, such as by moving the virtual object from a first position to a second position. For example, the user may move an object with his or her hand. This may be done in the AR/VR system virtually by determining that the hand has moved into a position coincident or adjacent to the object (e.g., using one or more sensors 200, which may be mounted on an AR/VR device, and which may be static or may be controlled to move), and causing the object to move in response. Virtual aspects may include virtual representations of real world objects, drop-down menus, text, and/or may include visual effects, such as lighting effects, etc.

The system and AR/VR device may provide an entirely virtual representation of an OR environment. As such, no portion of the real-world environment may be included in the systems and methods of the present invention.

The OR environment provided by the system may be viewable to one or more viewers, for example, each viewer using their own AR/VR device, and may include differences among views available for the one or more viewers while retaining some aspects as universal among the views. For example, a heads-up display may change between two views while virtual objects may be fixed to a real object or area in both views. Aspects such as a color of an object, lighting, or other changes may be made among the views without changing a fixed position of at least one virtual object. Such may be used to provide a more realistic representation of a virtual environment, and/or may be used to provide a different set of action responses. For example, one user may be designated as a trainer and another user may be designated as an observer (e.g., trainer).

The system may include rules to govern the behavior of virtual objects, such as subjecting a virtual object to gravity or friction, or may include other predefined rules that defy real world physical constraints (e.g., floating objects, perpetual motion, etc.).

According to certain aspects of the system, the OR environment may include a space outside of the operating room, such as a "sink room, and an operating room. In general, the scrubbing-in procedure occurs in the space outside of the operating room, and may include the 10 steps outlined above. Moreover, the gowning/gloving procedure generally occurs in the operating room (OR), and may include the 12 steps outlined above.

The system of the present invention may provide a visual, audible, or haptic feedback on the performance evaluation (e.g., alerts). Moreover, when the feedback is visual and/or audible, it may also provide a corrective instruction after an incorrectly executed action has been detected by the system (e.g., text instruction presented on the display, audible instruction, etc.).

The system of the present invention may be configured to provide a real-time performance score and/or a final performance score based on a cumulative performance evaluation.

According to certain aspects, the system may provide a virtual reality representation of the OR environment. As such, the processor-executable instructions comprise instructions to generate a virtual reality simulation of the operating room environment, and the performance metric may identify movement of the virtual objects in the operating room environment. Movement of the virtual objects in the operating room environment may be indicated by selections from the user, such as provided by user gestures, manual selection, and/or audible input of the user.

Detecting actions on objects within the augmented or virtual reality environment may include use of at least one sensor. The sensor(s) may detect actions of both real and virtual objects within the environment. These actions may be compared to a performance metric. For example, the performance metric may include data related to any of the steps detailed above (e.g. a length of time to properly wash hands, categories of sterile and non-sterile objects, proper steps in a gowning procedure, etc.). Thus, for example, if a user touches a non-sterile surface after washing their hands, or donning gloves, that action may be recorded and indicated in a performance evaluation.

Moreover, the augmented/virtual reality environment may include virtual versions of real objects, where the virtual object occupies the same space as the real object. Thus, actions on virtual versions of real objects in the augmented or virtual reality environment may be compared, and actions and interactions with these virtual versions may be evaluated to accurately change the appearance or other properties of the virtual objects as defined by pre-programmed properties. As such, visual signals related to a user's actions may be shown on the virtual versions of the real objects (e.g., change color of non-sterile/sterile objects, etc.).

This type of feedback may also be included in purely virtual environments. Thus, the appearance or properties of purely virtual objects, with no physical analog in the real environment, may be changed based upon actions and interactions with other purely virtual objects or real objects, as defined by their pre-programmed properties. This could include purely visual changes, movements, or other properties such as audio vocalizations.

Detection of actions and interactions may involve the use of wearable or freestanding sensors, such as cameras, infrared (IR) beacons, wireless beacons, and inertial measurement units. Some sensors may be attached to augmented reality devices worn by participants or users, or they may be attached to real objects and communicate with the system to provide additional information about the state of the real and virtual space relative to those objects, or they may be freestanding.

Recording the events transpiring in an augmented reality environment refers to a method of detecting and recording user actions such as body movement, and speech in addition to the passage of time, the visual or audio experience of participants, and the occurrence of pre-programmed events, and using that record to evaluate user performance based up on pre-determined metrics.

The sensor(s) may be communicatively coupled to a computer. The sensor(s) may be configured to provide data (e.g., image data, sensed data, six degrees of freedom data, etc.) to the computer. Furthermore, the sensor(s) may be configured to receive data (e.g., configuration data, setup data, commands, register settings, etc.) from the computer. The computer may include one or more processors, memory devices, and storage devices. The processor(s) may be used to execute software, such as the training software disclosed above, image processing software, sensor(s) software, and so forth. Moreover, the processor(s) may include one or more microprocessors, such as one or more "general-purpose" microprocessors, one or more special-purpose microprocessors and/or application specific integrated circuits (ASICS), or some combination thereof. For example, the processor(s) may include one or more reduced instruction set (RISC) processors.

The storage device(s) (e.g., nonvolatile storage) may include ROM, flash memory, a hard drive, or any other suitable optical, magnetic, or solid-state storage medium, or a combination thereof. The storage device(s) may store data (e.g., data corresponding to a training operation, video and/or parameter data corresponding to a training operation, etc.), instructions (e.g., software or firmware for the training system, the sensor(s), etc.), and any other suitable data.

The memory device(s) may include a volatile memory, such as random access memory (RAM), and/or a nonvolatile memory, such as read-only memory (ROM). The memory device(s) may store a variety of information and may be used for various purposes. For example, the memory device(s) may store processor-executable instructions (e.g., firmware or software) for the processor(s) to execute, such as instructions for a training simulation and/or for the sensor(s). In addition, a variety of control regimes for various training processes, along with associated settings and parameters may be stored in the storage device(s) and/or memory device(s), along with computer code configured to provide a specific output (e.g., feedback related to performance metric or evaluation, etc.) during operation.

The programs and systems of the present invention may be configured to work across many platforms (e.g., Android, iOS, Microsoft Windows, UNIX, etc.). Moreover, the presently disclosed software applications may use programming of one or both of the graphics processing unit (e.g., CUDA, DirectX or OpenCL) and the central processing unit to enhance the computational performance.

Active learning has been shown to be more effective than passive learning. As such, the methods and systems of the present invention provide improved means to learn various procedures, such as the scrubbing-in procedure, gowning/gloving procedure, and/or OR etiquette, by creating an active learning environment. Moreover, the methods and systems of the present invention provide an enjoyable and helpful means to learn these procedures, and provides all parties in the OR involved with the application/device—OR novices, OR experts, the patient, etc.—with a competitive advantage over OR rooms that have personnel that have not been trained by the methods and systems of the present invention. The novices will be better prepared for the OR, which will lead to a more sterile, comfortable OR with more fluid, efficient procedures. The improved sterility will decrease the risk of contamination of the patient, which improves patient outcomes and cost/time effectiveness (i.e. less adverse event reports/costs). The increased efficiency will make the surgery more cost effective due to the possible reduced time of the procedure. The improved comfort (due to the increased OR knowledge bases of the OR novices) will provide a less tense environment that ultimately reduces the overall stress of the OR for all parties involved.

The methods and systems disclosed herein may also find use beyond training, such as medical education, and medical certification. Additionally, the methods and systems of the present invention may be configured as games, wherein positive feedback may gain rewards and negative feedback may reduce reward (e.g., score).

As such, while specific embodiments of the invention have been described in detail, it should be appreciated by those skilled in the art that various modifications and alternations and applications could be developed in light of the overall teachings of the disclosure. Accordingly, the particular arrangements, systems, apparatuses, and methods disclosed are meant to be illustrative only and not limiting as to the scope of the invention.

What is claimed is:

1. A training system comprising:
  a non-transitory memory comprising processor-executable instructions; and
  a processor coupled to the non-transitory memory and configured to execute the processor-executable instructions, wherein the processor-executable instructions comprise instructions to:
    generate an augmented or virtual reality simulation of an operating room environment comprising an operating room and a space outside of the operating room;
    detect, using at least one sensor, an occurrence of an action within the operating room environment;
    compare the action to a performance metric; and
    generate, based at least in part on the comparing, a performance evaluation,
  wherein the performance metric identifies actions taken during a scrubbing-in procedure, and optionally, a gowning/gloving procedure, and
  wherein the scrubbing-in procedure comprises the following steps performed in the space outside of the operating room:
    removing jewelry from hands and arms;
    putting on a face mask and eye protection;
    taking and opening a pre-packaged scrub/nail kit
    moistening hands and arms with water from a faucet without touching the faucet
    using a bristled side of a brush from the pre-packaged scrub/nail kit to scrub nails;
    using a bristled end of the brush to scrub all surfaces of fingers and hands;
    using a sponge to scrub an entire length of one forearm, from wrist to elbow;
    using the sponge to scrub an entire length of contralateral forearm, from wrist to elbow:
    rinsing off both forearms allowing water to fall from wrists to elbows; and using back, butt, or hip to enter the operating room while keeping arms positioned up and away from torso.

2. The training system of claim 1, wherein the action within the operating room environment comprises a physical movement of a user of the system, a movement of a real object in the operating room environment, a movement of a virtual object in the operating room environment, or a combination thereof.

3. The training system of claim 1, further comprising:
a display in communication with the processor, wherein the display is configured to provide a visual representation of the operating room environment.

4. The training system of claim 3, wherein the display is further configured to provide a visual feedback of the performance evaluation.

5. The training system of claim 1, wherein the performance evaluation defines an aseptic quality of the scrubbing-in procedure, a speed of the scrubbing-in procedure, performance of all steps in the scrubbing-in procedure, performance of a proper order of the steps in the scrubbing-in procedure, or a combination thereof.

6. The training system of claim 1, wherein the performance evaluation defines an aseptic quality of the gowning/gloving procedure, a speed of the gowning/gloving procedure, performance of all steps in the gowning/gloving procedure, performance of a proper order of the steps in the gowning/gloving procedure, or a combination thereof.

7. The training system of claim 1, wherein the gowning/gloving procedure comprises:
entering the operating room environment with cleaned wet hands and arms in an elevated position, and approaching a scrub technician or nurse, taking care to avoid touching anything;
holding out first hand to accept a dry towel from the scrub technician or nurse;
drying second hand and arm using the first hand, from hand to elbow;
passing the towel to the second hand to dry the first hand and arm, from hand to elbow;
placing both hands and arms into sleeves of a gown, allowing fingertips to come through ends of sleeves, wherein the gown is held open by the scrub technician or nurse;
allowing a nonsterile nurse or circulator to tie a back of the gown using a first set of ties;
placing right hand into right glove, wherein the right glove is held open by the scrub technician or nurse;
placing left hand into left glove, wherein the left glove is held open by the scrub technician or nurse;
handing a second tie to the scrub technician or nurse, or to the nonsterile nurse or circulator;
rotating in gown with the scrub technician or nurse, or to the nonsterile nurse or circulator still holding the second tie;
re-grasping the second tie from the scrub technician or nurse, or to the nonsterile nurse or circulator; and
tying the second tie at front of the gown.

8. The training system of claim 1, wherein the system provides visual, audible, or haptic feedback on the performance evaluation during the scrubbing-in procedure, the gowning/gloving procedure when executed, or both.

9. The training system of claim 8, wherein the visual feedback, audible feedback, or both provide a corrective instruction after an incorrectly executed action.

10. The training system of claim 1, wherein the system provides a final performance score based on a cumulative performance evaluation.

11. The training system of claim 1, wherein the processor-executable instructions comprise instructions to generate a virtual reality simulation of the operating room environment, and the performance metric identifies movement of the virtual objects in the operating room environment.

12. The training system of claim 11, wherein movement of the virtual objects in the operating room environment are indicated by selections from a user of the system, wherein the selections are provided by user gestures, manual or audible input of the user, or a combination thereof.

13. A training method for a scrubbing-in procedure, the method comprising:
identifying, using a processor, a scrubbing-in procedure including a plurality of steps;
presenting, using an augmented reality display of an augmented reality device, a virtual representation of a sink room of an operating room suite;
querying a user for a first step in the scrubbing-in procedure;
determining whether the first step in the scrubbing-in procedure has been completed; and
in response to determining that the first step has been completed, presenting to the user a virtual representation of a subsequent step in the scrubbing-in procedure.

14. The method of claim 13, further comprising:
before determining the first step in the scrubbing-in procedure has been completed:
determining that the first step is not being performed, or that the first step is being performed improperly; and
displaying an alert using the augmented reality display indicating that an error.

15. The method of claim 13, wherein the plurality of steps in the scrubbing-in procedure are ordered, and include:
removing jewelry from hands and arms;
putting on a face mask and eye protection;
taking and opening a pre-packaged scrub/nail kit;
moistening hands and arms with water from a faucet without touching the faucet;
using a bristled side of a brush from the pre-packaged scrub/nail kit to scrub nails;
using a bristled end of the brush to scrub all surfaces of fingers and hands;
using a sponge to scrub an entire length of one forearm, from wrist to elbow;
using the sponge to scrub an entire length of contralateral forearm, from wrist to elbow;
rinsing off both forearms allowing water to fall from wrists to elbows; and
using back, butt, or hip to enter the operating room while keeping arms positioned up and away from torso.

16. The method of claim 13, further comprising, after the plurality of steps in the scrubbing-in procedure are complete:
querying a user for a first step in a gowning/gloving procedure, wherein the gowning/gloving procedure is presented on the augmented reality display of the augmented reality device as a virtual representation of an operating room;
determining whether the first step in the gowning/gloving procedure has been completed; and
in response to determining that the first step has been completed, presenting to the user a virtual representation of a subsequent step in the gowning/gloving procedure.

17. The method of claim 16, further comprising:
before determining the first step in the gowning/gloving procedure has been completed:
determining that the first step is not being performed, or that the first step is being performed improperly; and
displaying an alert using the augmented reality display indicating that an error.

18. The method of claim 16, wherein the plurality of steps in the gowning/gloving are ordered, and include:
entering the operating room environment with cleaned wet hands and arms in an elevated position, and approaching a scrub technician or nurse, taking care to avoid touching anything;
holding out first hand to accept a dry towel from the scrub technician or nurse;
drying second hand and arm using the first hand, from hand to elbow;
passing the towel to the second hand to dry the first hand and arm, from hand to elbow;
placing both hands and arms into sleeves of a gown, allowing fingertips to come through ends of sleeves, wherein the gown is held open by the scrub technician or nurse;
allowing a nonsterile nurse or circulator to tie a back of the gown using a first set of ties;
placing right hand into right glove, wherein the right glove is held open by the scrub technician or nurse;
placing left hand into left glove, wherein the left glove is held open by the scrub technician or nurse;
handing a second tie to the scrub technician or nurse, or to the nonsterile nurse or circulator;
rotating in gown with the scrub technician or nurse, or to the nonsterile nurse or circulator still holding the second tie;
re-grasping the second tie from the scrub technician or nurse, or to the nonsterile nurse or circulator; and
tying the second tie at front of the gown.

19. A training system comprising:
a non-transitory memory comprising processor-executable instructions; and
a processor coupled to the non-transitory memory and configured to execute the processor-executable instructions, wherein the processor-executable instructions comprise instructions to:
generate an augmented or virtual reality simulation of an operating room environment;
detect, using at least one sensor, an occurrence of an action within the operating room environment;
compare the action to a performance metric; and
generate, based at least in part on the comparing, a performance evaluation,
wherein the performance metric identifies actions taken during a gowning/gloving procedure comprising:
entering the operating room environment with cleaned wet hands and arms in an elevated position, and approaching a scrub technician or nurse, taking care to avoid touching anything;
holding out first hand to accept a dry towel from the scrub technician or nurse;
drying second hand and arm using the first hand, from hand to elbow;
passing the towel to the second hand to dry the first hand and arm, from hand to elbow;
placing both hands and arms into sleeves of a gown, allowing fingertips to come through ends of sleeves, wherein the gown is held open by the scrub technician or nurse;
allowing a nonsterile nurse or circulator to tie a back of the gown using a first set of ties;
placing right hand into right glove, wherein the right glove is held open by the scrub technician or nurse;
placing left hand into left glove, wherein the left glove is held open by the scrub technician or nurse;
handing a second tie to the scrub technician or nurse, or to the nonsterile nurse or circulator;
rotating in gown with the scrub technician or nurse, or to the nonsterile nurse or circulator still holding the second tie;
re-grasping the second tie from the scrub technician or nurse, or to the nonsterile nurse or circulator; and
tying the second tie at front of the gown.

* * * * *